US010165943B2

(12) United States Patent
Maughan et al.

(10) Patent No.: US 10,165,943 B2
(45) Date of Patent: Jan. 1, 2019

(54) OPHTHALMIC METHOD AND APPARATUS FOR NONINVASIVE DIAGNOSIS AND QUANTITATIVE ASSESSMENT OF CATARACT DEVELOPMENT

(71) Applicants: David Maughan, Burlington, VT (US); Alexander Kochis, Seattle, WA (US); Guy Kennedy, Underhill, VT (US)

(72) Inventors: David Maughan, Burlington, VT (US); Alexander Kochis, Seattle, WA (US); Guy Kennedy, Underhill, VT (US)

( * ) Notice: Subject to any disclaimer, the term of this patent is extended or adjusted under 35 U.S.C. 154(b) by 0 days.

(21) Appl. No.: 15/652,274

(22) Filed: Jul. 18, 2017

(65) Prior Publication Data
US 2018/0014726 A1 Jan. 18, 2018

Related U.S. Application Data

(60) Provisional application No. 62/363,569, filed on Jul. 18, 2016.

(51) Int. Cl.
*A61B 3/12* (2006.01)
*A61B 3/117* (2006.01)

(52) U.S. Cl.
CPC .................. *A61B 3/1176* (2013.01)

(58) Field of Classification Search
CPC ......... A61B 3/103; A61B 3/1208; A61B 3/12; A61B 3/1015; A61B 3/1005; A61B 3/1176
USPC ........................................................ 351/211
See application file for complete search history.

(56) References Cited

U.S. PATENT DOCUMENTS

| | | | | |
|---|---|---|---|---|
| 4,368,958 A | * | 1/1983 | Buget | G02C 13/003 33/200 |
| 6,315,412 B1 | * | 11/2001 | Snodderly | A61B 3/02 351/200 |
| 2017/0055831 A1 | * | 3/2017 | Miwa | A61B 3/14 |

* cited by examiner

*Primary Examiner* — William R Alexander
*Assistant Examiner* — Henry Duong

(57) ABSTRACT

An optoelectronic apparatus and method is provided. The application of which provides a quantitative index of cataract opacity in the human eye to help the clinical practitioner screen patients for referral for cataract lens replacement surgery. The invention includes at least one adjustable intensity optical reference light source selected from the group consisting of a green light source and a red-light source. The invention also includes at least one fixed intensity cataract absorption light source, selected from the group consisting of a blue light source, an indigo light source, and a violet light source.

8 Claims, 4 Drawing Sheets

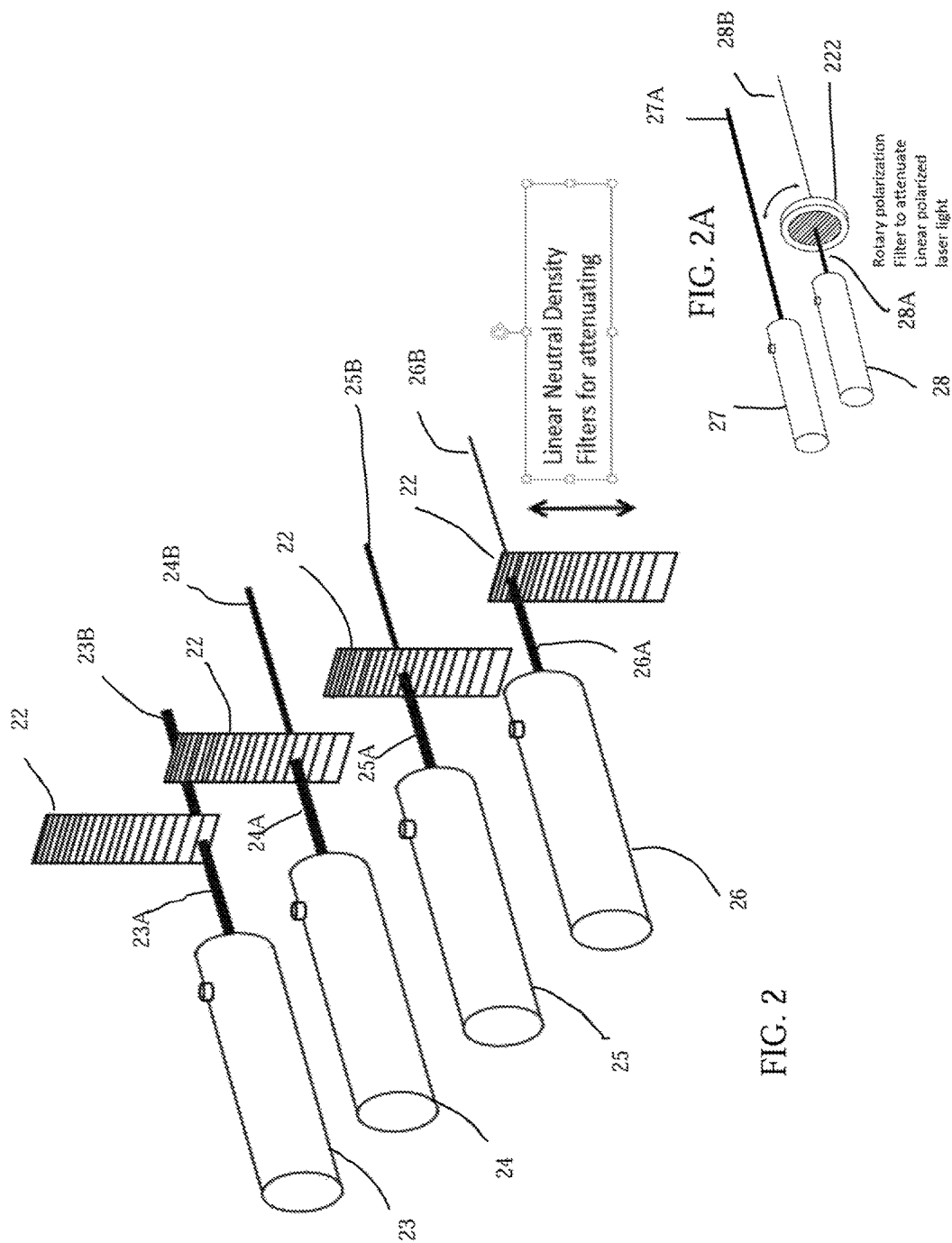

OPHTHALMIC METHOD AND APPARATUS FOR NONINVASIVE DIAGNOSIS AND QUANTITATIVE ASSESSMENT OF CATARACT DEVELOPMENT

CROSS-REFERENCE TO RELATED APPLICATIONS

The present application is related to, claims the earliest available effective filing date(s) from (e.g., claims earliest available priority dates for other than provisional patent applications; claims benefits under 35 USC § 119(e) for provisional patent applications), and incorporates by reference in its entirety all subject matter of the following listed application(s) (the "Related Applications") to the extent such subject matter is not inconsistent herewith; the present application also claims the earliest available effective filing date(s) from, and also incorporates by reference in its entirety all subject matter of any and all parent, grandparent, great-grandparent, etc. applications of the Related Application(s) to the extent such subject matter is not inconsistent herewith:

U.S. provisional patent application 62/363,569, entitled "OPHTHALMIC METHOD AND APPARATUS FOR NONINVASIVE DIAGNOSIS AND QUANTITATIVE ASSESSMENT OF CATARACT DEVELOPMENT", naming David W. Maughan as inventor, filed 18 Jul. 2016.

BACKGROUND

1. Field of Use

The present invention generally relates to noninvasive determination of disease states. More particularly, the present invention relates to a method and apparatus for noninvasively determining an ocular disease state, and for noninvasively determining the rate of development of this ocular disease state.

2. Description of Prior Art (Background)

The healthy human eye contains a clear lens that focuses light rays onto the retina. Clouding of the lens is called a cataract. A cataract causes decreased vision by interfering with the normal transmission of light through the eye's clear lens onto the retina. The degree of visual loss is determined by cloudiness of the lens and the location in the lens where the cloudiness occurs. Cataracts are uncommon in children and young adults; however nearly everyone develops cataracts as they age due to cumulative oxidative damage (stress) to the lens. Approximately 70% of people develop cataracts by 75 years of age according to the American Academy of Ophthalmology.

Lens abnormalities include: senile nuclear cataract (the most common age-related cataract), senile conical cataract (also an age-related cataract), congenital cataract, embryonic nuclear cataract, anterior polar cataract, lenticonus cerulean opacities, sub capsular cataract, posterior subcapsular cataract, cortical cataract, mature cataract, shield cataract, traumatic cataract, bilateral lens distortion, lenticulocorneal adhesion, Christmas tree cataract (indicative of myotonic dystrophy) and sunflower cataract (indicative of Wilson disease).

A person with a mature cataract, which significantly impairs visual function, may be treated by surgically extracting the impaired lens of the person and replacing it with either an intraocular lens or an extraocular lens. However, the condition cannot be addressed until the cataract is properly diagnosed or determined.

Many different methods and apparatus are known in the prior art to help determine the existence or extent of a cataract. These methods and apparatus generally make the determination based either on visual acuity tests or on an analysis of light exiting the eye of the patient. However, due to various anomalies these prior art approaches may not be optimum indicators of a cataract. In the case of visual acuity tests which depend upon light reaching the retina, the use of high contrast letters or figures may enable the patient to recognize the letters and figures and thus "pass" the visual acuity test regardless of a cataract condition.

Similarly, another test compares a photograph of a person's lens to a standardized series of photographs showing lenses with different degrees of cataract formation in different parts of the lens. However, the resulting photographic images depend upon back scattered light from the lens. Because the back scattered light may not correlate highly with the location of the cataract and what the patient sees, a clinician using the photographs as the basis of an analysis will not be able to accurately determine the effect of opacities upon the patient's visual function and accordingly the patient may "pass" or may "fail" the test incorrectly. In U.S. Pat. No. 4,863,261, issued to J. Flammer, entitled "Method of and Apparatus for Measuring the Extent of Clouding of the Lens of a Human Eye," light exiting the eye, i.e. "back scattered" light, is analyzed with respect to incident radiation to determine the extent of clouding of the lens.

Cataract detection using scattering techniques is described in Benedek et al., in U.S. Pat. No. 4,993,827 for "Method for Detecting Cataractogenesis", issued Feb. 19, 1991. Benedek et al. collects and determines the intensity of light scattered from a measurement location in the lens and compares this value to the intensity of light scattered by a normal clear lens to determine the degree of cataractogenesis at the specific measurement location.

Another scattering detection technique is described in Taratuta et al., in U.S. Pat. No. 5,072,731 for "Apparatus for Detecting Cataractogenesis Using Quasielastic Light Scattering", issued Dec. 17, 1991. Taratuta et at analyzes the light scattered from the lens using an autocorrelation function, or the power spectrum, to separate the light fluctuation into two components: one caused by fast diffusing proteins and one caused by slow diffusing protein aggregates. The data is then compared to reference curves to determine the degree of cataractogenesis.

In each of the above back scattering techniques, low intensity light must be incident upon the eye in order to avoid damage to the eye. Because of the limited incident intensity, only a small amount of light is reflected back to a photomultiplier of limited quantum efficiency for measurement. The limited amount of reflected light and limited quantum efficiency of the photomultiplier make accurate analysis difficult.

Kandel et al. in U.S. Pat. No. 5,908,394 describes a method of quantifying cataract disease states in the human lens, which builds on a centuries-old observation that colors are perceived differently due to differential light absorption in the lens; in particular, light toward the blue and violet wavelength of the spectrum is absorbed more than light toward the green and red wavelengths of the spectrum. This phenomenon is responsible for various degrees of color "blindness" that have long been observed by people with cataracts.

In Kandel et al. the subject is asked to determine when 1) two non-monochromatic light spots are identical in "color, hue, and saturation" as the mix of colors is varied, with 2) intensity remaining equal. That is, color mix is varied, but light intensity is not. The preferred embodiment for the light source specified is a Tungsten Halogen bulb that provides white light to various color filters (with fairly broad bands); attenuation of light is achieved by a neutral density "electro-optic polarizer followed by a variable pi-cell".

Kontadakis et al, J. Cataract Refract. Surg. 2011: Kontadakis et al. evaluated human lens opacity using heterochromatic flicker photometry (HFP), a standard method for assessing macular pigment optical density. Kontakakis et al. employed a commercial instrument (MPS 9000 QuantiEye Macular Pigment Screener, Tinsley Ophthalmic Instruments, Inc.) equipped with light emitting diodes (LED) of 465 nm (blue) and 530 nm (green) wavelengths, that flickered in counter-phase on a white-light pedestal. Opacity (ocular media density), determined from the comparative attenuation of the blue test light versus the green reference light, was assessed by instructing the subject to minimize or eliminate the perception of flicker, by adjusting the intensity of the blue test light while keeping the intensity of the green reference light constant.

As with the Kandel's invention, the Kontadakis et al. application is an adaptation of a well-known observation that the absorption properties of tinted intraocular lenses resemble that of aging human lenses; while un-tinted intraocular lenses resemble the lower levels of blue light attenuation found in younger lenses.

Teikari et al., J. Opt. Soc. Am. A. 2012: Teikari et al. describes a further refinement of the use of heterochromatic flicker photometry (HFP). Light attenuation in the human lens was approximated by fitting absorbance differences, measured using a custom-built HFP instrument with a mathematical model of ocular media age-dependency.

The commercial LEDs (LedEngin, Inc. & Philips, Inc.) in Teikari et al. have wavelength peaks at 405 nm and 530 nm and is based on the well-known phenomenon (of differential blue versus green light absorbance in the human lens).

Van Best et al, Invest. Opthalmol. Vis. Sci. 1985: Van Best et al. 1985 describes another method of determining the properties of blue-green light transmission through the human lens using standard techniques of autoflurophotometry. Lens transmission is calculated from peak autofluorescence values (comparing peak autofluorescence values in the anterior and posterior part of the lens) in diabetic patients and healthy controls. Autofluorescence is measured with computer flurorophotometer (Fluorotron Master of Coherent Radiation, Inc.). The light wavelengths are set by the instrument's color filters, which had fairly broad bands with peaks at 490 nm and 530 nm.

Thus, a need exists for an improved, noninvasive, ocular disease state determination. The present invention meets this need by providing a subject with an apparatus where there are two monochromatic light spots and the subject determines when the two monochromatic lights spots become equally bright as the intensity of one light spot is varied. That is, color, hue and saturation are not varied as in Kandel et al., nor is color alternatively presented in counter-phase as in Kontadakis et al and Teikari et al.

BRIEF SUMMARY

One embodiment of the present invention is an ophthalmic optoelectronic method and apparatus that, with direct feedback from the subject, provides a (semi) quantitative measure of cataract opacity using the relative absorption of two different wavelengths of light from monochromatic sources (blue or violet light versus green or red light).

In one embodiment (A), lasers are the light source; in another (B), light-emitting diodes are the light source; in a third (C), a light-emitting display (liquid crystals, organic light emitting diodes, or polymer light emitting diodes) is the light source. In all embodiments, a subjective match of the intensity of light of different wavelengths yields a quantitative measure for relative opacity of a cataract in situ, thus allowing an assessment of the progression of the disease and the need for cataract replacement lens surgery.

The invention is also directed towards series of graphics spaced at intervals selected to discriminate between normal vision and vision impaired by the presence of a cataract. The graphics may be displayed on a digital display device such as a computer, digital display device, smart phone, etc. One or more groups of graphics exhibit a short wavelength test light (e.g., blue or violet) and another one or more graphic groups exhibit a longer wavelength reference light (e.g. red). A patient adjusts the intensity of the reference light to match, substantially, the subject's perceived intensity of the test light. The difference between the intensities relates to the presence or the advancement of a cataract. The digital device stores the patient's test information to provide a historical analysis of the patient's cataract progression.

The invention is also directed towards an ophthalmic apparatus for noninvasive diagnosis and quantitative assessment of cataract development. The apparatus includes at least one intensity adjustable optical reference light source selected from the group consisting of a green light source and a red-light source. The apparatus also includes at least one fixed intensity optical test light source selected from the group consisting of a blue light source, an indigo light source, and a violet light source.

In accordance with another embodiment of the invention a method for noninvasive diagnosis and quantitative assessment of cataract development is provided. The method includes providing a cataract testing device and calibrating the cataract testing device. Calibrating the cataract testing device includes providing a cataract absorption light (CAL) source at a first preset intensity CALI and providing a reference light (RL) source at a second preset intensity RLI greater than the first preset intensity. Next, observing RLI and CALI simultaneously via a cataract free lens and decreasing RLI in predetermined calibration steps (CS) to substantially equal CALI. The method includes providing the reference light (RL) at the second preset intensity RLI greater than the first preset intensity and observing RLI and CALI simultaneously via a cataract lens. Next, decreasing RLI in predetermined absorption steps (AS) to substantially equal CALI and calculating a cataract index of opacity $O=AS-CS$.

The invention is also directed towards a method for noninvasive diagnosis and quantitative assessment of cataract development. The method includes providing and calibrating a cataract testing device. Calibrating the cataract testing device includes providing a cataract absorption light (CAL) source at a first preset intensity CALI, wherein the CAL source is selected from the group consisting of a blue light source, an indigo light source, and a violet light source. The method also includes providing a reference light (RL) source at a second preset intensity RLI greater than the first preset intensity, wherein the RL source is selected from the group consisting of a green light source, and a red-light source. Next the method includes observing RLI and CALI simultaneously via a cataract free lens; and decreasing RLI in predetermined calibration steps (CS) to substantially equal CALL, wherein decreasing RLI in predetermined calibration steps further comprises decreasing RLI with a least one filter selected from the group consisting of a linear neutral density filter and a rotary polarization filter. The method also includes observing RLI and CALI simultaneously via a cataract lens and decreasing RLI in predetermined absorption steps (AS) to substantially equal CALI. Next the method provides calculating a cataract index of opacity O=AS−CS and saving the cataract index of opacity 0 in a medical health record.

BRIEF DESCRIPTION OF THE DRAWINGS

The subject matter which is regarded as the invention is particularly pointed out and distinctly claimed in the claims at the conclusion of the specification. The foregoing and other objects, features, and advantages of the invention are apparent from the following detailed description taken in conjunction with the accompanying drawings in which:

FIG. 2 is an illustration of a system for employing the method shown in FIG. 1;

FIG. 2A is an illustration of an alternate system for attenuating light in the system shown in FIG. 2;

DETAILED DESCRIPTION

The following brief definition of terms shall apply throughout the application:

The term "comprising" means including but not limited to, and should be interpreted in the manner it is typically used in the patent context;

The phrases "in one embodiment," "according to one embodiment," and the like generally mean that the particular feature, structure, or characteristic following the phrase may be included in at least one embodiment of the present invention, and may be included in more than one embodiment of the present invention (importantly, such phrases do not necessarily refer to the same embodiment);

If the specification describes something as "exemplary" or an "example," it should be understood that refers to a non-exclusive example; and If the specification states a component or feature "may," "can," "could," "should," "preferably," "possibly," "typically," "optionally," "for example," or "might" (or other such language) be included or have a characteristic, that particular component or feature is not required to be included or to have the characteristic.

Figure 1:
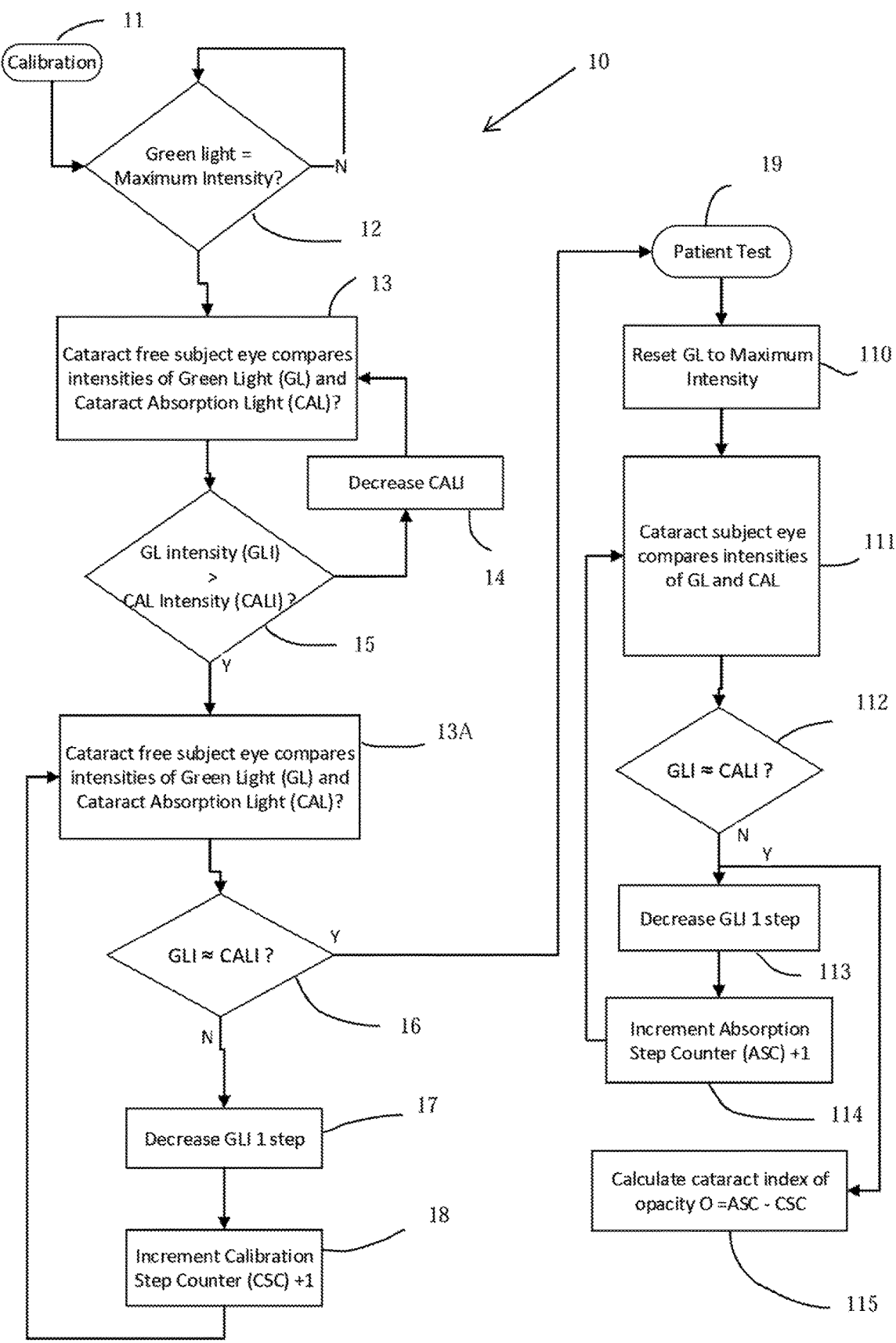
FIG. 1 is a flow chart for one method of detecting cataracts in accordance with the invention described herein.

Referring to FIG. 1 there is shown a flow chart of one method 10 for implementing features of the present invention. Steps 11-18 calibrate the invention to minimize differences in the perceived intensity of green light (490-570 nm) or red light (620 nm-780 nm) compared with the cataract absorption light intensity (CALI) that may be apparent with a cataract free lens. It will be understood that the CAL may be any suitable light, such as, for example, a blue light (i.e., 440 nm-490 nm, or a violet light (i.e., 400 nm-420 nm), or an indigo light (i.e., 420 nm-440 nm). The perceived differences or variances may be due to different factors such as differences in intrinsic light intensity related to power output variances, power degradation, or differences in transmissibility (T) of light through a clear lens.

Still referring to FIG. 1, A green light (GL) source is set to its maximum intensity 12. It will be understood that a red light (RL) source may be used in place of GL. A cataract free subject eye compares 13 the GL intensity (GLI) against the intensity of the CAL. If the GLI is not greater 15 than the CALI, and the GLI has been set to maximum 12, then the CALI is decreased 14 until the GLI is greater than CALI 15. It will be understood that throughout the patient test, the CALI is held as the reference light and not adjusted further.

Step 13A and step 16 compares the GLI to the CALI. If the intensities are approximately equal then the patent test 19 is started. If the intensities are not approximately equal the GLI is decreased by one step. The resulting fractional change in transmittance of GLI is measured relative to its initial setting; that is, the extent to which the intensity of the green light is reduced in order to match the perceived intensity of the blue light. The OD or T of the corresponding filter(s) steps establishes the standard (null point) against which further changes in perceived intensity of the blue light is measured.

Still referring to FIG. 1, it will be understood that decreasing GLI by one step 17 may be decreasing GLI by any suitable measure. (See, for example, FIG. 2, where the light intensities may be reduced by using a linear graduated neutral density filter 22.) The transmittance range of the filter is, approximately, 100% at one end of the filter, i.e., step 0, to 0% transmittance at the other end of the filter, step x. The transmittance graduation steps of the filter from step 0 to step x may be any suitable number of graduating transmittance steps. For example, the filter graduation steps may be 21 steps (from step 0 to step 20), where each step corresponds to a 5% of transmittance blocking such that step 0 corresponds to 100% transmittance (no blocking), step 10 corresponds to 50% transmittance blocking, and step 20 corresponds to 0% transmittance (light is fully blocked). It will also be understood that light intensity may be reduced by with rotating filters (see. FIG. 2A), or electronic control (see FIG. 3).

Still referring to FIG. 1, once the GLI has been calibrated the patient test starts 19. The GL is reset to its maximum 110 and the cataract subject eye compares 111 the GL and CAL intensities. If the GLI is approximately equal to the CALI 112, then the cataract index of opacity O is calculated 115 as the Absorption Step Counter (ASC)—the Calibration Step Counter (CSC).

Still referring to FIG. 1, if the GLI is not substantially equal to CALI then the GLI is decreased 113, as described earlier in the calibration steps. The ASC is incremented by one and the patient again compares 111 the GLI and CALI until the GLI is substantially equal 112. When the GLI substantially equals the CALI the cataract index of opacity (O) is calculated 115.

For example, using a blue CAL for one test subject, two steps (0 to 2) of the GLI filter was required to reduce the GLI to match CALI subject's healthy eye. Seven steps (0 to 7) were required to reduce the GLI to match the CALI in the cataract eye. Similarly, four steps (0 to 4) of the GLI filter were required to reduce the GLI to match a violet CALI in the subject's healthy eye, and 10 steps (0 to 10) in the cataract eye, i.e., consistent with the wave-length dependent transmissibility of light through a cataract lens.

The difference in graduated steps is denoted as an index of opacity, O, where Oblue is determined by ASC-CSC 115 using blue light CAL or Oviolet using violet light CAL. In the example, the index of opacity is Oblue is 5 (=7−2) and Oviolet is 6 (=10−4), indicating an advanced cataract. Gradations in opacity index may be any suitable gradation, limited by the gradation and range of the neutral density filter and ability of the subject to perceive light intensity differences.

In many cases the patient does not have a (control) healthy eye which serves as a within-patient standard by which the opacity of a cataract, Oblue and Oviolet, can be calculated as shown in FIG. 1. Thus, in many patients, the steps required to reduce the GLI to match the CALI as in a healthy eye, is determined by using the average values from many system measurements conducted by subjects without cataracts.

For example, using the prototype system shown in FIG. 2A, a subject with cataracts required 5 steps (0 to 5) of the GLI filter (v.2, FIG. 2A) to reduce the GLI to match that of the blue CALI in one eye, and 5 steps (0 to 5) to match the blue CALI in the other eye. Using a violet CAL, six steps (0 to 6) were required to reduce the GLI to match that of the violet CALI light in both the first and second eye, consistent with the wave-length dependent transmissibility of light through a cataract lens. In this example, the reference GLI standard for the system used to calculate 0 was the average number of steps required to reduce the GLI to match that of the blue CALI (2 steps) or violet CALI (3 steps) by three cataract free subjects. Thus, Oblue is 3 (=5−2) and Oviolet were 3 (=6−3), indicating cataracts, but, not as pronounced as in the first example.

Referring also to FIG. 2 there is shown one system for employing the method shown in FIG. 1. Light sources 23-26 may be any suitable combination of reference light sources, e.g., a red or green light source, and any suitable combination of CAL. For example, in one application (i), a green (or red) laser is aligned alongside a blue laser. In a more complex application (ii), a green (or red) laser is aligned alongside both a blue and a violet laser. In the most complex application iii), all four lasers are aligned side-by-side. Light 23A, 24A, 25A, and 26A emitted by light sources 23-26 is intensity attenuated 23B, 24B, 25B, 26B by linear graduated neutral density filters 22, discussed above.

The intensity of the light sources 23-26 is attenuated by a graduated neutral density filter 22, allowing optical density (OD) or transmittance (T) to be altered. In one embodiment, the filters 22 may be constructed of plastic (as in a plastic film strip) or glass (as in a rotating glass filter—see FIG. 2A). In another embodiment, the filters may be constructed of liquid crystals, where light is altered electronically. Using this system, for example, the index of opacity is Oblue is 5 (=7−2) and Oviolet is 6 (=10−4), indicating an advanced cataract.

Referring also to FIG. 2A there is shown an alternate system for employing the method shown in FIG. 1. Light source 27 emits CAL. Reference light source 28 emits light 28A which is intensity attenuated by rotary filter 222 to transmit attenuated intensity light 28B.

Figure 3A:
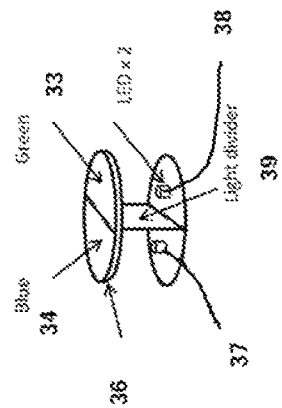
FIG. 3A is an illustration of a system for generating a reference light and a cataract absorption light (CAL) in the system shown in FIG. 3.
Figure 3:
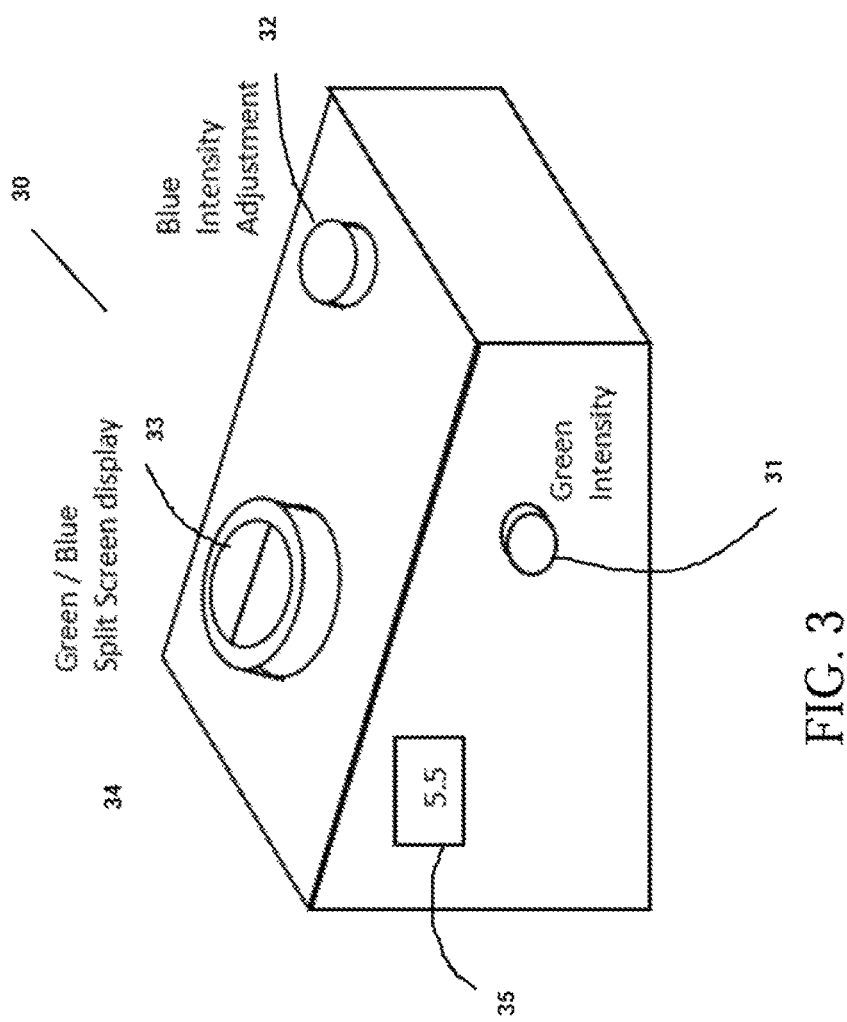
FIG. 3 is an illustration of an alternate system for employing the method shown in FIG. 1.

Referring also to FIG. 3 and FIG. 3A there is shown another system 30 embodiment for employing the method shown in FIG. 1. System 30 employs light emitting diodes (LEDs) 37, 38. Light from an LED is nearly monochromatic (narrow bandwidth of light), and is available in red, green, blue, violet, pink, yellow/orange, and white. In alternate embodiments, the transparent glass can be colorized, or pigmented, such that white light from LEDs 37, 38, entering the colorized transparent glass 36 is emitted as blue CAL 34 and GLI 33 (or any suitable colored CAL such as violet or indigo, and any suitable colored reference light such as red light). Light divider 39 separates the LEDs 37, 38. The patient views light from the colored (or white) LEDs 37, 38, transmitted through a transparent glass 36 and adjusts the intensities as described in FIG. 1. System 30 includes an optical index O calculator and display 35.

The use of LEDs 37, 38 allows for versatile presentation of lights of different wavelengths. For example, LEDs of many colors can be activated and displayed in various combinations of reference light (e.g., GL) and CAL.

Figure 4:
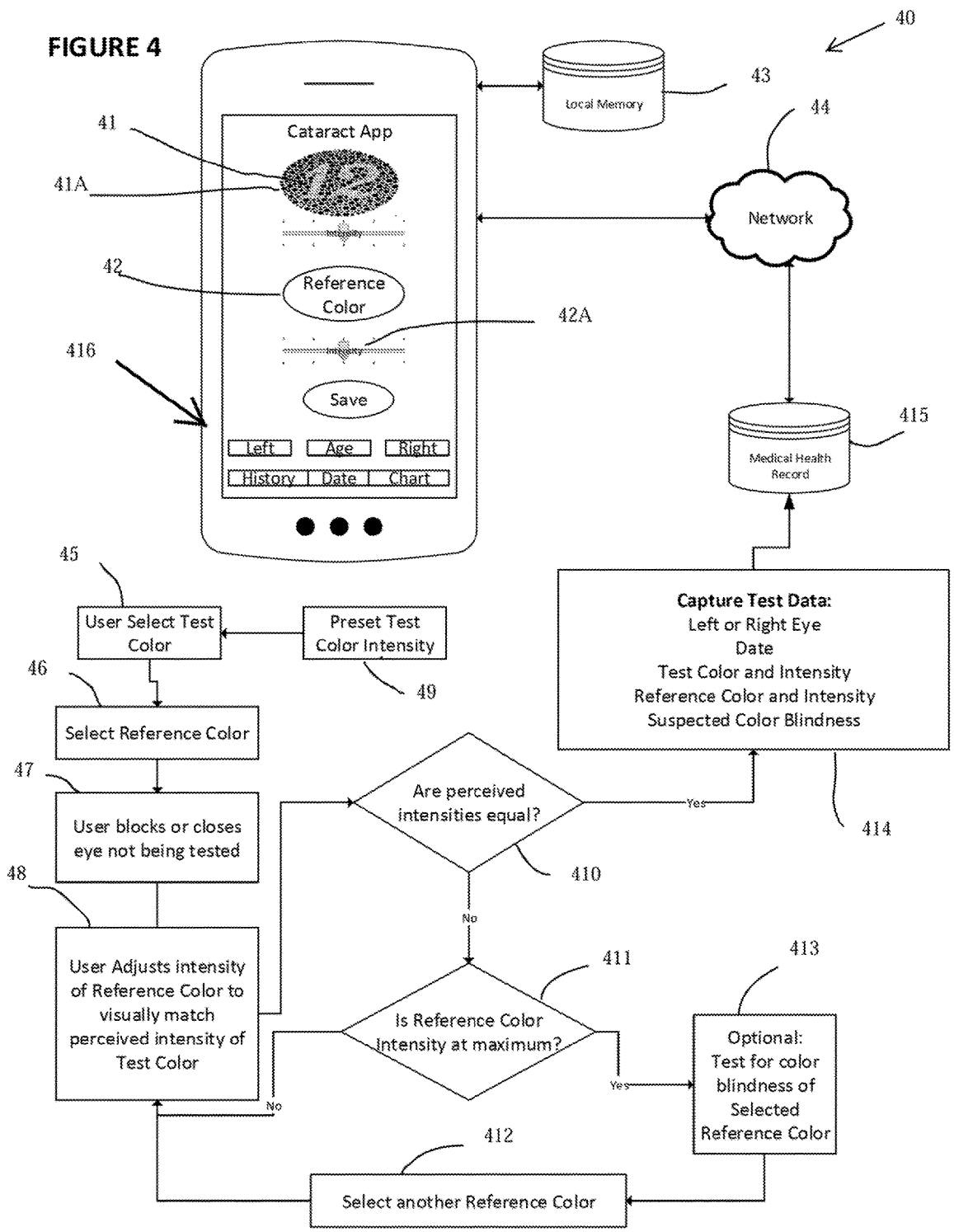
FIG. 4 is a system flow chart for one method of detecting cataracts and color blindness in a mobile device in accordance with the invention shown in FIG. 1.

Referring also to FIG. 4 there is shown a flow chart for one method 40 of detecting cataracts and color blindness in a mobile device in accordance with the method shown in FIG. 1. Device 416 may be any suitable device such as a tablet, cell phone, or other mobile device. Step 49 presets test color, e.g., the blue light CAL 41 to a preset intensity. The user selects 45 a test color 41. The test color or CAL is displayed as a number or letter 41 within random colored dots 41A. If the patient cannot see the number or letter 41 the patient may be color blind to that color and selects another test color.

The patient or user selects 46 a reference color 42, e.g., a green light GL. The patient blocks the eye not being tested 47 and adjusts 48 intensity 42A until the intensity of the reference color 42 substantially matches 410 the intensity of the test color 41. If the reference color intensity is maximum 411 and the patient or user has not perceived the intensities of the reference color and test color as substantially equal then the patient may be tested 413 for color blindness of the reference color and selects another reference color 412.

Still referring to FIG. 4, once the patient perceives equal intensities of the reference color 42 and the test color 41 the test data is captured 414 and the optical index O is calculated as described earlier. The test data may be stored for later retrieval and analysis in a local medical record 415 or in a network or cloud storage 44.

It will be appreciated that an important feature of the invention discussed herein is the means (whether mechanically or electronically) to modulate the intensity of light from each light source. As discussed above, cataracts absorb blue (and to an even greater extent) violet light more than a cataract-replacement lens or a cataract-free lens, and the method relies on the subject to adjust the intensity of light from the green or red-light source to match that of the blue or violet light source. The difference in intensity (in OD units or other graduated scales) is the measure, or index, of relative opacity of the cataract compared with a clear lens.

In one test using the prototype system shown in FIGS. 3 and 3A, (using green and blue LEDs), 10 subjects (ages 23-82), where the intensity of the green LED used as the reference light was sequentially altered before each cataract test in which the intensity of the blue test LED was varied. The data was acquired sequentially from lowest to highest intensity with the same relative green intensities for each subject. At the lowest value of the green reference LED, Oblue averaged 1.40 for subjects >50 years and 0.04 for subjects <50 years, given a mean reference standard value obtained from two subjects with artificial lens. At the highest value of the green reference LED, Oblue averaged 1.8 for subjects >50 years and 0.02 for subjects <50 years, given the same mean reference standard value (two subjects with artificial lens). The differences appear to be most significant at the brighter readings, It will be appreciated that criteria derived from the invention discussed herein may be used for establishing a referral for CLRS. For example, in the system shown in FIG. 2 any eye with an Oblue above 3.0 and an Oviolet above 4.0 may be classified as indicating CLRS and require referral to a specialist. Values below these thresholds but above 2.0 may require retesting every year to track the cataract development, given the patient's baseline results. Similarly, the cataract measuring systems shown in FIG. 3 and FIG. 4 may be used to develop cataract baselines unique to the measuring system.

It should be understood that the foregoing description is only illustrative of the invention. Thus, various alternatives and modifications can be devised by those skilled in the art without departing from the invention. Accordingly, the present invention is intended to embrace all such alternatives, modifications and variances that fall within the scope of the appended claims.

What is claimed is:

1. A method for noninvasive diagnosis and quantitative assessment of cataract development, the method comprising:
   providing a cataract testing device;
   calibrating the cataract testing device, wherein calibrating the cataract testing device comprises:
      providing a cataract absorption light (CAL) source at a first preset intensity (CALI);
      providing a reference light (RL) source at a second preset intensity RLI greater than the first preset intensity;
      observing RLI and CALI simultaneously via a cataract free lens; and
      decreasing RLI in predetermined calibration steps (CS) to substantially equal CALI.

2. The method as in claim 1 wherein the CAL source is selected from the group consisting of a blue light source, an indigo light source, and a violet light source.

3. The method as in claim 1 wherein the RL source is selected from the group consisting of a green light source, and a red-light source.

4. The method as in claim 1 wherein decreasing RLI in predetermined calibration steps further comprises decreasing RLI with at least one shift in position of at least one first linear neutral density filter.

5. The method as in claim 1 wherein decreasing RLI in predetermined calibration steps further comprises decreasing RLI with at least one shift in position of at least one rotary polarization filter.

6. The method as in claim 1 further comprising:
   providing the reference light (RL) at the second preset intensity RLI greater than the first preset intensity;
   observing RLI and CALI simultaneously via a cataract lens;
   decreasing RLI in predetermined absorption steps (AS) to substantially equal CALI; and
   calculating a cataract index of opacity O=AS−CS.

7. The method as in claim 6 further comprising observing the CAL within random colored dots.

8. The method as in claim 7 further comprising saving the index of opacity 0 in a medical health record.

* * * * *